United States Patent [19]

Baumgartner et al.

[11] Patent Number: 5,735,850
[45] Date of Patent: Apr. 7, 1998

[54] FASTENING SYSTEM FOR PEDICEL SCREWS

[75] Inventors: Walter Baumgartner, Wil; Stefan Freudiger, Bremgarten, both of Switzerland

[73] Assignees: Sulzer Medizinaltechnik AG, Winterthur; Protek AG, Muensingen-Bern, both of Switzerland

[21] Appl. No.: 593,959

[22] Filed: Jan. 30, 1996

[30] Foreign Application Priority Data

Feb. 17, 1995 [EP] European Pat. Off. ............ 95810106

[51] Int. Cl.$^6$ .................................................. A61B 17/56
[52] U.S. Cl. ............................ 606/61; 606/70; 606/71; 606/73
[58] Field of Search ........................ 606/60, 61, 69, 606/70, 71, 72, 73

[56] References Cited

U.S. PATENT DOCUMENTS

| | | | |
|---|---|---|---|
| 2,443,363 | 6/1948 | Townsend et al. | 606/71 |
| 2,780,223 | 2/1957 | Haggland | 606/69 |
| 4,696,290 | 9/1987 | Steffee | 606/69 |
| 5,129,899 | 7/1992 | Small et al. | 606/71 |
| 5,269,784 | 12/1993 | Mast | 606/71 |
| 5,344,421 | 9/1994 | Crook | 606/70 |
| 5,487,741 | 1/1996 | Maruyama et al. | 606/69 |

FOREIGN PATENT DOCUMENTS

| | | | |
|---|---|---|---|
| 860756 | 9/1981 | U.S.S.R. | 606/61 |
| WO 93/01772 | 2/1993 | WIPO . | |

*Primary Examiner*—Michael Buiz
*Assistant Examiner*—Julian W. Woo
*Attorney, Agent, or Firm*—Townsend and Townsend and Crew LLP

[57] ABSTRACT

The invention discloses a fastening system for pedicel screws anchorable in different vertebrae. The spherical screw heads lie in spherical shells of apertured counter-bodies. The counter-bodies have planar support surfaces which lie on a supporting link in the region of elongate holes. A screw element is provided in the axial direction of each pedicel screw and is pivotably journalled at the supporting link with a spherical support surface arranged in the region of the elongate hole. The pedicel screws are generally skewed relative to one another and can, when account is taken of the nature of the bone, be rigidly connected to the supporting links via the screw elements due to the fact that the support surfaces can be clamped against one another in a self-locking manner on pedicel screws which are positioned inclined relative to the support surfaces.

21 Claims, 4 Drawing Sheets

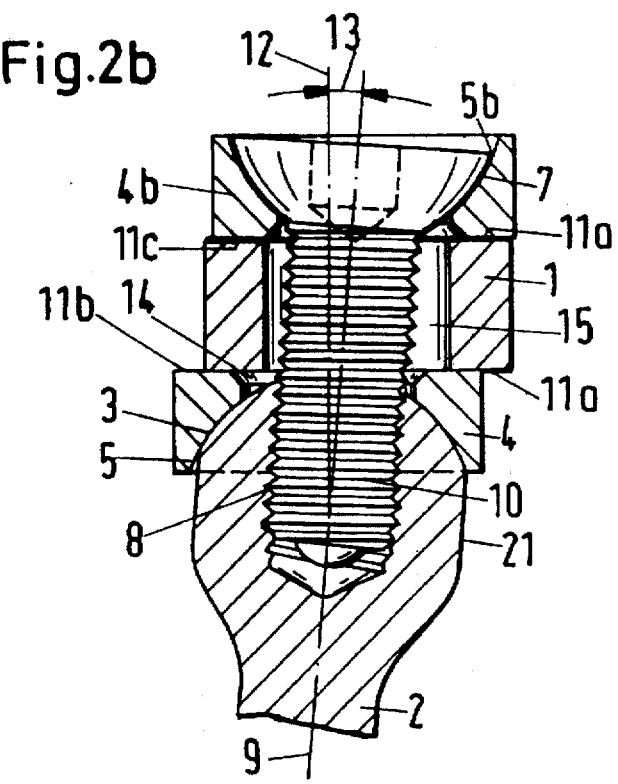
Fig.2b
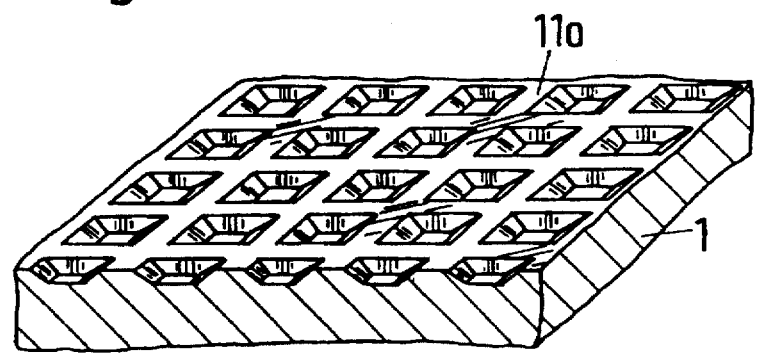
Fig.7
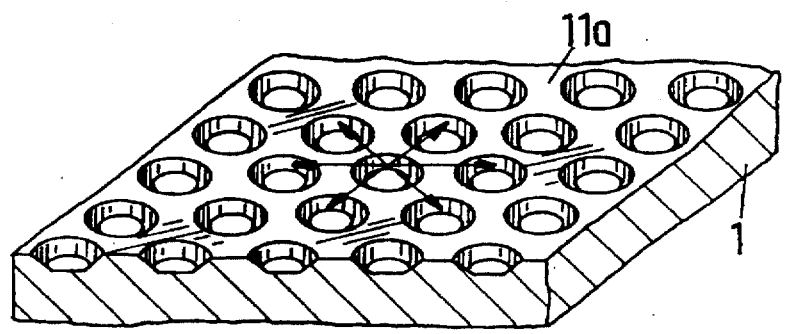

FASTENING SYSTEM FOR PEDICEL SCREWS

BACKGROUND OF THE INVENTION

The invention relates to a fastening or connection system for pedicel screws anchorable in different vertebrae. Such a fastening system has an apertured supporting link; pedicel screws having a head with a spherical support surface; a perforated counter-body which butts against the supporting link and has on its opposite side a concave support surface with an aperture; and a screw element which has a spherical support surface and is clamped against the supporting link and the counter-body with a thread in the pedicel screw extending in the direction of an axis of the pedicel screw.

As a rule, pedicel screws screwed into different vertebrae serve as a basis for the securing of support elements and carriers between the pedicel screws for providing positional correction between vertebrae or for relieving intervertebral disks and providing intervertebral stiffening reinforcement.

A fastening system for pedicel screws is disclosed in U.S. Pat. No. 5,129,899. It discloses a planar carrier provided with a slot-shaped aperture extending over its length, with the carrier extending over two or more vertebrae. The two arms of the carrier separated by the slot have a toothed segment on their outer side surfaces on which underlay disks can be positioned at varying separations in the longitudinal direction, the underlay disks having cut-away side cheeks with a corresponding toothed segment. The overlapping side cheeks have the advantage that they prevent the two carrier arms from splaying apart since the carrier arms and the underlying disks are clamped against spherical support surfaces on the pedicel screw and securing nuts. The arrangement has the disadvantage that the axes of the pedicel screws have to lie in a common plane so that, on securing of the connecting carrier to a self-supporting construction, no lasting torque acting on the anchorage of the pedicel screws can be produced in the carrier.

SUMMARY OF THE INVENTION

It is an object of the invention to provide a simple fastening or connection between pedicel screws which are skewed relative to one another. The screw has a shaft that is anchorable in the head of the pedicel screw. A concave support surface of the counter-body butts against the spherical part on the head of the pedicel screw. On the opposite side, the counter-body has a planar surface that is freely displaceable on a planar support surface of the supporting link to secure the pedicel screw through the counter-body to the supporting link such that an angle is formed between the axis of the pedicel screw and the perpendicular of the planar support surface. In the inclined position relative to the perpendicular of the planar support surface, the counter-body and the supporting link are connectable in a self-locking manner. A tension-free connection or linkage is thereby produced. This arrangement has the advantage that self-tapping pedicel screws can be used which, as they are screwed in, can still change their axial alignment in response to variations in the bone tissue hardness to achieve an optimum anchorage. The alignment differences as well as the differences in the alignment of the bone pieces for the anchorage of the pedicel screws are compensated for by the fastening system.

To to bridge the differences in separation between the heads of two or more pedicel screws anchored in different vertebrae, connecting carriers or supporting links are provided which have elongate holes and cylindrically extending support surfaces along the direction of their longitudinal axes for the spherical support surfaces of the screw elements, with the spherical and cylindrical radii corresponding to one another. Consistent with a modular system, the supporting links are provided such that their elongate holes have different average separations so that an entire range of separations of the pedicel screw heads can be covered. A further variation is provided in that, in a supporting link, the planar support surfaces in the region of the elongate holes for the counter-body can be parallel to one another, parallel and offset, or non-parallel. A further variation is comprised such that the longitudinal axes of the elongate holes can be offset relative to one another in the perpendicular projection onto the plane of a support surface. To eliminate the need for stocking additional supporting links for these last two variations, the regions of the supporting links between the two elongate holes are weakened to such an extent that they can be bent with tools in the operating room into a corresponding transitional form between the support surfaces. Since the axis of each pedicel screw can be inclined in any direction by an angle relative to the perpendicular of the planar support surface, the exactness demanded of the deformation of the supporting link and the number of different supporting links needed can be held within reasonable limits. Each pedicel screw achieves a self-locking connection supported by the form between the head of the pedicel screw and the supporting link. In other words, a coarse stepping is possible. The self-locking is generally increased by roughening up at least one of the mutually paired support surfaces or by providing a microstructure with projecting points in order to achieve a form-locked connection via plastic deformation.

A further measure consists of transmitting onto the spherical support surface on the head of a pedicel screw and via the concave support surface of the counter-body as much as possible of the bending moment between the supporting link and the pedicel screw which will occur later under load. This is achieved by forming the counter-body as a ring with its dome being underdimensioned relative to the spherical surface of the pedicel screw, i.e. having a smaller radius. The sphere, which initially sits on the outer edge of the dome, is pressed into the dome when the two parts are pressed together and is elastically strained outwardly due to the wedge action of the sphere until practically the entire surface of the dome contacts the sphere. In this position, the microstructures of the two surfaces have the maximum mutual engagement and a connection is achieved which is correspondingly secure against rotation in all directions.

In a further embodiment of the invention the permissible pivotable range of the pedicel screws away from the perpendicular of the planar support surface on the supporting link is substantially increased by an interpenetrating microstructure provided in the form-locked connection from the supporting link and counter-body. The support surfaces can mutually engage with one another as a result of the repetition of their structure in a fine pattern and can be displaced in small increments in at least two directions. To then release the connection to the microstructure, a lifting out and, subsequent to the displacement, a reengagement into the engaged position are necessary to allow the transmission of lateral forces. Typical patterns can be, on the one support surface, regularly arranged pyramids with a base area of squares or rhombuses (because their manufacture is particularly simple, for example by milling or grinding) wherein, the form can be produced in the same manner on the other surface by a pressing tool which produces the counter surfaces via form reversal on pressing. Cones or another body in the same pattern can also be used instead of pyramids. The advantage of the inclined form of the interpenetrating microstructures is that they remain displaceable relative to one another in the common planar support surface under the action of the weight of the supporting link or counter part themselves and nevertheless form a solid connection against a pressing force applied inclined relative to the support surface.

In a further arrangement, the elongate holes on the supporting links are countersunk and, for this, a further counter-body to the screw element is provided on the side remote from the pedicel screw. The spherical supporting surface of the further counter-body corresponds to the concave support surface of the counter-body. As decribed above, the bearing support surfaces also have an interpenetrating microstructure. The variations of the supporting link described above are also possible.

BRIEF DESCRIPTION OF THE DRAWINGS

FIG. 2b is a schematic view of an enlarged section through an arrangement with two counter-bodies which contact on either side on the elongate hole of the supporting link;

FIG. 7 is a schematic view of enlarged microstructures for the support surfaces between the supporting link and counter part with the counterforms shown as they would arise from a pressing tool.

DESCRIPTION OF THE PREFERRED EMBODIMENTS

Figure 1:
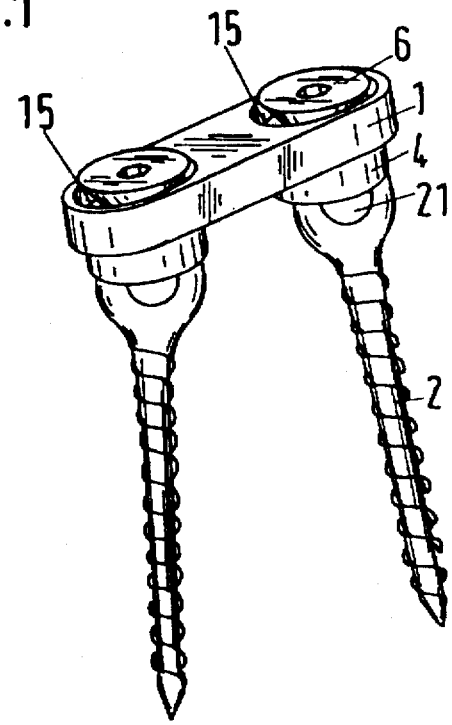
FIG. 1 is a schematic illustration of the connection between two pedicel screws which are skewed relative to one another.

The Figures show a fastening system for pedicel screws 2 anchorable in different vertebrae. The spherical screw heads 3 lie in spherical shells 5 of apertured counter-bodies 4. The counter-bodies 4 have planar support surfaces 11b which lie on a supporting link 1 in the region 11a of elongate holes 15. A screw element 6 is provided in the axial direction 9 of each pedicel screw 2 and is pivotably journalled at the supporting link with a spherical support surface 7 arranged in the region of the elongate hole 15. The pedicel screws 2 are in general skewed to one another and can, when account is taken of the nature of the bone, be rigidly connected to the supporting links via the screw elements 6 due to the fact that the support surfaces 11a, 11b can be clamped against one another in a self-locking manner on pedicel screws 2 which are positioned inclined relative to the support surfaces 11a, 11b.

Figure 2A:
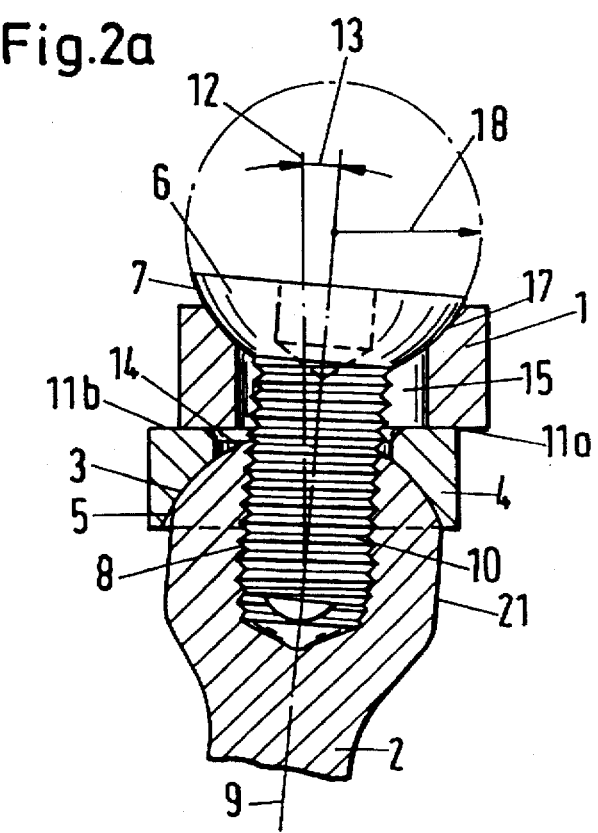
FIG. 2a is a schematic view of an enlarged section through the head of a pedicel screw and its connection to a supporting link in accordance with FIG. 1.
Figure 3:
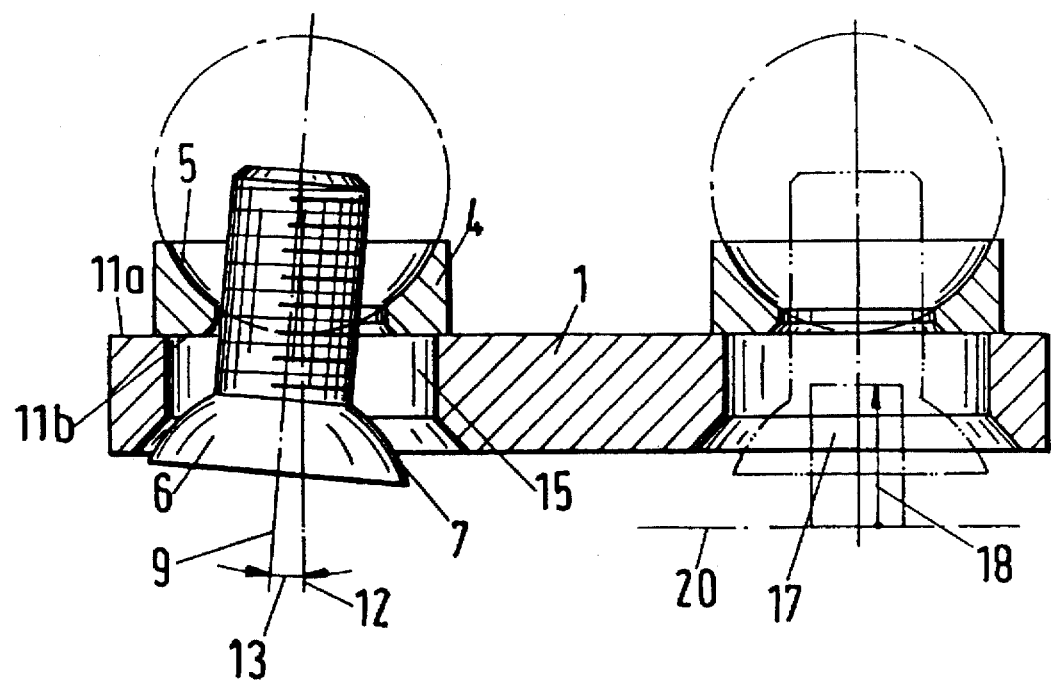
FIG. 3 is a schematic view of an enlarged longitudinal section through a supporting link of FIG. 1.
Figure 4:
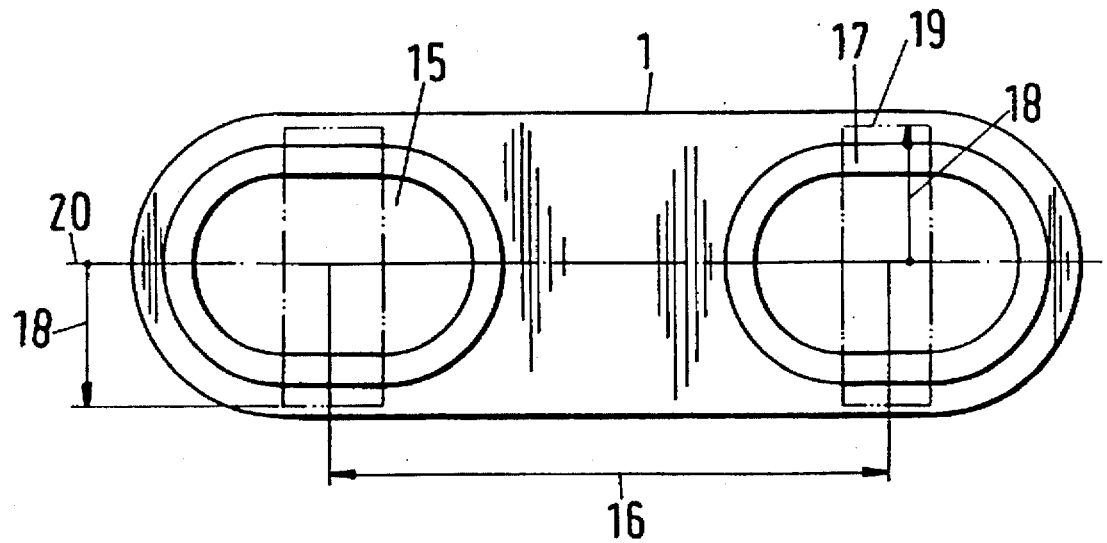
FIG. 4 is a schematic plan view of the supporting link of FIG. 3.
Figure 5:
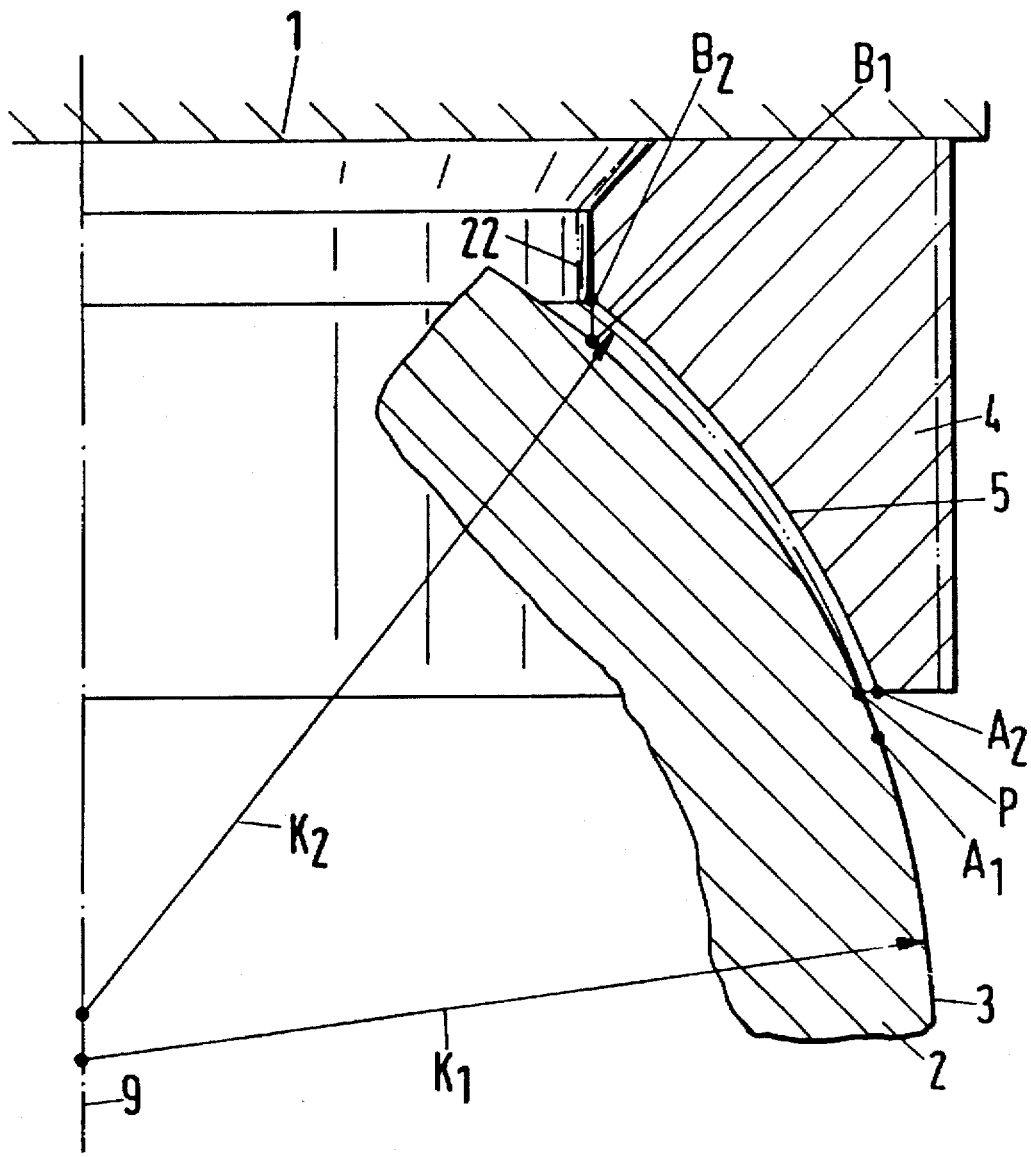
FIG. 5 is a greatly enlarged schematic diagram of the opening out of an underdimensioned counter-body due to the action of the spherical support surface of a pedicel screw.

FIG. 1 shows a fastening system having two pedicel screws 2. The screws are skewed relative to one another and are each connected with screws 6 and counter-bodies 4 to a supporting link 1. The supporting link comprises elongate holes 15 with an average distance selected to correspond approximately to the separation between the pedicel screw heads, for example 25 mm. In FIG. 2a, the supporting link 1 in the region of the elongate hole 15 has a flat or planar support surface 11a on which the similarly planar support surface 11b of the counter-body sits. A screw 6 can be screwed into the head of the pedicel screw in the direction of the axis 9 of the pedicel screw 2. The axis 9 extends inclined by an angle 13 relative to a perpendicular 12 of the support surfaces 11a, 11b. The head of the pedicel screw 2 has a spherical shape 3 and butts against a concave support surface 5 of the counter-body 4. The head of the screw element 6 also has a spherical support surface, the radius 18 of which corresponds to the radius of a cylindrical surface piece 17 in the elongate hole 15 of the support element 1. In the inclined position away from the perpendicular 12, the spherical head 3 and the dome 5 as well as the spherical support surface 7 and the cylindrical surface 17 can rotate relative to one another whereas the support surfaces 11a, 11b can be displaced relative to one another in the plane. Now, as soon as a tensioning force is applied by the screw 6, the planar support surfaces 11a, 11b would move back once again if it were not for the fact that their connection is self-locking. A supporting link 1 with two elongate holes 15 is shown in FIGS. 3 and 4 with the holes being arranged separated from one another by an average distance 16. The elongate holes each have two surface pieces 17 formed corresponding to a cylinder 19 having its axis 20 extending in the longitudinal direction of the supporting link and having a radius 18 corresponding to that of the spherical support surface 7 on the screw element 6. This can also be seen in FIG. 2. The concave support surface 5 in the counter-body 4 is undersize relative to the spherical support surface 3 of the pedicel screw 2. In the greatly exaggerated representation of FIG. 5, the spherical support surface 3 with radius K1 is introduced into the counter-body in the direction of the axis 9 of the pedicel screw 2 until it butts against contour line 22 of radius K2 at the point P, this contour line 22 not yet being widened out. In this position, pivoting of the axis 9 is still not possible. As the screw element 6 is drawn in, the counter-body 4 is elastically widened out and the points A1, B1 of the spherical surface are displaced to the points A2, B2 on the dome surface in order to clamp the entire dome surface 5. The dome surface is sand-blasted and has a roughened-up surface with projecting points which penetrate into the spherical surface on deformation and thus render large bending moments between the pedicel screw and the counter-body transmissible.

The situation for the planar support surfaces 11a, 11b in the FIGS. 2a and 3 is similar, the support surfaces also being sand-blasted in order to prevent a relative sliding between the surfaces under biasing. Due to the fact that the microstructure of the surfaces interpenetrate, a self-locking action arises which permits angular deviations 13 of the pedicel screws away from the perpendicular 12. This effect can be amplified by providing the support surfaces 11a, 11b with a repeating interpenetrating microstructure. FIG. 7 shows microstructures of surfaces 11a in which the recesses have the form of negative forms to the pyramid or conical stumps and repeat in at least two different directions. If the repetition steps are selected to be correspondingly small, a fine pattern for the mutual anchoring of the surfaces 11a, 11b under biasing is provided.

The inclination of the projections permits a displacement in the plane 11 in the unloaded condition. Projections in the form of pyramids which are the counterpieces to the above representation of FIG. 7 are particularly simple to manufacture both as parts themselves and as embossing tools for producing the form reversal.

Since the spherical dome of the support surface 5 and the spherical support surface 3 practically retain their center of rotation, the aperture in the counterbody 4 can be selected such that the screw element 6 can only be pivoted with the pedicel screw 2 in an angle 13 corresponding to the self-locking of the surfaces 11a, 11b under biasing.

Figure 6:
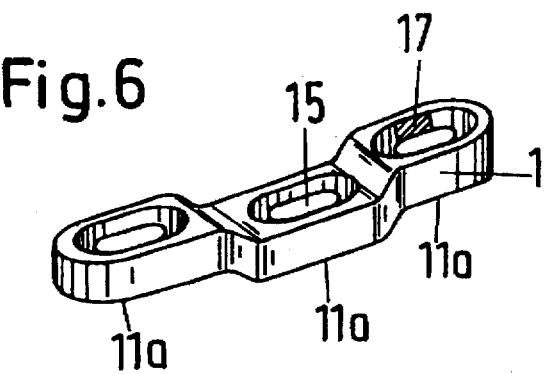
FIG. 6 is a schematic view of a supporting link with three elongate holes having associated support surfaces arranged at different levels.

FIG. 6 shows a supporting link 1 with a bent form which has three countersunk elongate holes 15 with the countersinks having cylindrical surface pieces 17 for the engagement of the screw elements. The intermediate pieces between two elongate holes are formed such that a plastic bending is still possible in the operating room using tools for roughly aligning the support surfaces 11a. This can for example be performed by a reduction of the cross-section. In such a case it is advantageous when the planes of the support surfaces 11a only have recesses as the microstructure.

FIG. 2b shows a screw 6 screwed into the head of the pedicel screw 2 which has a longer threaded part 8 in comparison to that of FIG. 2a. A counter-body 4b lies under the pedicel screw 2 and comprises a concave support surface 5 directed to the spherical support surface 7 of the pedicel screw as well as a planar support surface 11c directed towards the supporting link 1. The concave support surface 5 can also be underdimensioned in this case in order to produce biasing. The support surfaces can also have an interpenetrating microstructure here as well.

We claim:

1. A fastening system for pedicel screws anchorable in different vertebrae of different orientations, said fastening system comprising:

a supporting link including a plurality of apertures each having a receiving surface and a perpendicular and a planar supporting link surface which is normal to the perpendicular;

a plurality of counter-bodies each having a planar counter-body surface butting against one of the planar supporting link surfaces in a self-locking manner, a concave support surface, and a counter-body aperture extending between the planar counter-body surface and the concave support surface, the planar counter-body surface being adjustable relative to the planar supporting link surface to define a degree of inclination relative to the perpendicular;

a plurality of pedicel screws each having a head with a spherically shaped pedicel support surface and defining a pedicel screw axis, the head including an internal threaded portion extending from the spherically shaped pedicel support surface along the pedicel screw axis, the spherically shaped pedicel support surface cooperating with the concave support surface of one of the counter-bodies; and a plurality of screw elements each having a spherical support surface and an external threaded portion extending along the pedicel screw axis of one of the plurality of pedicel screws, the external threaded portion extending through one of the plurality of apertures of the supporting link and the counter-body aperture of one of the plurality of counter-bodies, and engaging the internal threaded portion of the pedicel screw to secure the pedicel screw to the supporting link and the counter-body, the spherical support surface cooperating with the receiving surface at the aperture of the supporting link, the pedicel screw axis being oriented skewed relative to the perpendicular by a degree equal to the degree of inclination.

2. The fastening system of claim 1, wherein the plurality of apertures of the supporting link comprise a plurality of countersunk elongated holes which are separable by a distance corresponding to an average separation between two neighboring vertebrae.

3. The fastening system of claim 2, wherein the receiving surface of each of the plurality of countersunk elongated holes of the supporting link comprises portions of a cylindrical surface corresponding to a cylinder with a radius equal to the radius of the spherical support surface of one of the plurality of screw elements, the cylinder having an axis that extends in the direction of elongation of the elongated holes.

4. The fastening system of claim 1, wherein the concave support surface of each of the counter-bodies is undersized compared to the spherically shaped pedicel support surface of the pedicel screw which is in cooperation with the concave support surface, the concave support surface undergoing spreading deformation to come into fitting contact with the spherically shaped pedicel support surface.

5. The fastening system of claim 1, wherein the concave support surface of each of the counter-bodies engages the spherically shaped pedicel support surface which is in cooperation with the concave support surface securely with strained microstructure.

6. The fastening system of claim 1, wherein at least one of the spherical support surfaces and the receiving surface which is in cooperation with the spherical support surface is roughened or is provided with a microstructure to increase the friction therebetween.

7. The fastening system of claim 1, wherein at least one of the spherically shaped pedicel support surface and the concave support surface which is in cooperation with the spherically shaped pedicel support surface is roughened or is provided with a microstructure to increase the friction therebetween.

8. The fastening system of claim 1, wherein the planar supporting link surface and the planar counter-body surface which is butted against the planar supporting link surface contact each other with an interpenetrating microstructure for self-locking, the planar counter-body surface being displaceable relative to the planar supporting link surface in small steps by separation and reengagement of the planar counter-body surface and the planar supporting link surface.

9. The fastening system of claim 1, wherein the supporting link comprises different bent supporting link portions having non-parallel planar support surfaces, each of the bent supporting link portions having at least one of the plurality of apertures.

10. The fastening system of claim 1, wherein the supporting link comprises different offset supporting link portions that are offset relative to each other, each of the offset supporting link portions having at least one of the plurality of apertures.

11. The fastening system of claim 1, wherein the perpendiculars of the plurality of apertures of the supporting link are offset relative to each other in the plane of the planar supporting link surface.

12. A fastening system for pedicel screws anchorable in different vertebrae of different orientations, said fastening system comprising:

a supporting link including a plurality of apertures each having a first planar supporting link surface and a perpendicular and a second planar supporting link surface which is normal to the perpendicular;

a plurality of first counter-bodies each having a first planar counter-body surface butting against one of the first planar supporting link surfaces in a self-locking manner, a first concave support surface, and a first counter-body aperture extending between the first planar counter-body surface and the first concave support surface, the first planar counter-body surface being adjustable relative to the first planar supporting link surface;

a plurality of second counter-bodies each having a second planar counter-body surface butting against one of the second planar supporting link surfaces in a self-locking manner, a second concave support surface, and a second counter-body aperture extending between the second planar counter-body surface and the second concave support surface, the second planar counter-body surface being adjustable relative to the second planar supporting link surface;

a plurality of pedicel screws each having a head with a spherically shaped pedicel support surface and defining a pedicel screw axis, the head including an internal threaded portion extending from the spherically shaped pedicel support surface along the pedicel screw axis, the spherically shaped pedicel support surface cooperating with the second concave support surface of one of the second counter-bodies; and a plurality of screw elements each having a spherical support surface and an external threaded portion extending along the pedicel screw axis of one of the plurality of pedicel screws, the external threaded portion extending through the first counter-body aperture of one of the plurality of first counter-bodies, one of the plurality of apertures of the supporting link and the second counter-body aperture of one of the plurality of second counter-bodies, and engaging the internal threaded portion of the pedicel screw to secure the pedicel screw to the first counter-body, the supporting link and the second counter-body, the spherical support surface cooperating with the first concave support surface at the aperture of the first counter-body, the pedicel screw axis being oriented skewed relative to the perpendicular.

13. The fastening system of claim 12, wherein the apertures of the supporting link comprise a plurality of countersunk elongated holes which are separable by a distance corresponding to an average separation between two neighboring vertebrae.

14. The fastening system of claim 12, wherein the second concave support surface of each of the second counterbodies is undersized compared to the spherically shaped pedicel support surface of the pedicel screw which is in cooperation with the concave support surface, the second concave support surface undergoing spreading deformation to come into fitting contact with the spherically shaped pedicel support surface.

15. The fastening system of claim 12, wherein the second concave support surface of each of the second counterbodies engages the spherically shaped pedicel support surface which is in cooperation with the second concave support surface securely with strained microstructure.

16. The fastening system of claim 12, wherein at least one of the spherical support surface and the first concave support surface which is in cooperation with the spherical support surface is roughened or is provided with a microstructure to increase the friction therebetween.

17. The fastening system of claim 12, wherein at least one of the spherically shaped pedicel support surface and the second concave support surface which is in cooperation with the spherically shaped pedicel support surface is roughened or is provided with a microstructure to increase the friction therebetween.

18. The fastening system of claim 12, wherein the first planar supporting link surface and the first planar counter-body which is butted against the first planar supporting link surface contact each other with an interpenetrating microstructure for self-locking, the first planar counter-body surface being displaceable relative to the first planar supporting link surface in small steps by separation and reengagement of the first planar counter-body surface and the first planar supporting link surface.

19. The fastening system of claim 12, wherein the second planar supporting link surface and the second planar counter-body which is butted against the second planar supporting link surface contact each other with an interpenetrating microstructure for Self-locking, the second planar counter-body surface being displaceable relative to the second planar supporting link surface in small steps by separation and reengagement of the second planar counter-body surface and the second planar supporting link surface.

20. The fastening system of claim 12, wherein the supporting link comprises different offset supporting link portions that are offset relative to each other, each of the offset supporting link portions having at least one of the plurality of apertures.

21. The fastening system of claim 12, wherein the perpendicular the plurality of apertures of the supporting link are offset relative to each other in the plane of the planar supporting link surface.

* * * * *